(12) United States Patent
Kana et al.

(10) Patent No.: US 9,114,023 B2
(45) Date of Patent: Aug. 25, 2015

(54) INTERBODY FUSION DEVICE WITH SNAP ON ANTERIOR PLATE AND ASSOCIATED METHODS

(75) Inventors: Richard Kana, Lexington, TX (US); Kevin Dunworth, Dripping Springs, TX (US); John Rossman, Austin, TX (US); Larry Khoo, Studio City, CA (US); Zachary Smith, Chicago, IL (US)

(73) Assignee: SpineSmith Partners, L.P., Austin, TX (US)

(*) Notice: Subject to any disclaimer, the term of this patent is extended or adjusted under 35 U.S.C. 154(b) by 0 days.

(21) Appl. No.: 13/506,565

(22) Filed: Apr. 27, 2012

(65) Prior Publication Data
US 2012/0277872 A1    Nov. 1, 2012

Related U.S. Application Data

(63) Continuation-in-part of application No. 12/018,703, filed on Jan. 23, 2008, now Pat. No. 8,795,373, and a continuation-in-part of application No. 11/759,219, filed on Jun. 6, 2007, now Pat. No. 8,273,127.

(60) Provisional application No. 61/517,870, filed on Apr. 27, 2011, provisional application No. 60/981,414, filed on Oct. 19, 2007.

(51) Int. Cl.
*A61F 2/44*      (2006.01)
*A61B 17/86*      (2006.01)
(Continued)

(52) U.S. Cl.
CPC .............. *A61F 2/4465* (2013.01); *A61F 2/447* (2013.01); *A61B 17/8042* (2013.01); *A61B 17/86* (2013.01); *A61F 2/30744* (2013.01); *A61F 2/4611* (2013.01); *A61F 2002/2817* (2013.01); *A61F 2002/2835* (2013.01); *A61F 2002/302* (2013.01); *A61F 2002/305* (2013.01); *A61F 2002/30131* (2013.01); *A61F 2002/30352* (2013.01); *A61F 2002/30372* (2013.01); *A61F 2002/30373* (2013.01); *A61F 2002/30383* (2013.01); *A61F 2002/30387* (2013.01); *A61F 2002/30397* (2013.01); *A61F 2002/30482* (2013.01); *A61F 2002/30504* (2013.01); *A61F 2002/30507* (2013.01); *A61F 2002/30517* (2013.01); *A61F 2002/30578* (2013.01); *A61F 2002/30604* (2013.01); *A61F 2002/30607* (2013.01);
(Continued)

(58) Field of Classification Search
CPC ....... A61F 2/442; A61F 2/4455; A61F 2/446; A61F 2220/0025
USPC ..................... 606/246–249; 623/17.11–17.16
See application file for complete search history.

(56) References Cited

U.S. PATENT DOCUMENTS

2006/0074488 A1*   4/2006   Abdou ........................ 623/17.11
2006/0085071 A1*   4/2006   Lechmann et al. ........ 623/17.11
2006/0235518 A1*   10/2006   Blain ......................... 623/17.11

*Primary Examiner* — Ellen C Hammond
*Assistant Examiner* — Christina Negrellirodrigue
(74) *Attorney, Agent, or Firm* — Winstead PC (57) ABSTRACT

A method and apparatus is provided for use in spinal fusion procedures. An interbody fusion device has a first piece that is a load bearing device designed to bear the axial loading from the end plates of adjacent vertebrae. A second piece of the interbody fusion device is a retention device whose function is to prevent migration of the load bearing device. One or more fasteners secure the retention device to the vertebrae above and below the load bearing device. The fasteners cause the end plates of the vertebrae to compress the end plates to the load bearing device to facilitate proper fusion. The device includes a snap in mechanism for coupling the first piece to the second piece.

9 Claims, 12 Drawing Sheets (51) Int. Cl.
  *A61F 2/30*   (2006.01)
  *A61F 2/28*   (2006.01)
  *A61B 17/80*  (2006.01)
  *A61F 2/46*   (2006.01)

(52) U.S. Cl.
  CPC .......... *A61F2002/30616* (2013.01); *A61F 2002/30774* (2013.01); *A61F 2002/30782* (2013.01); *A61F 2002/30904* (2013.01); *A61F 2002/4475* (2013.01); *Y10T 29/49* (2015.01)

INTERBODY FUSION DEVICE WITH SNAP ON ANTERIOR PLATE AND ASSOCIATED METHODS

CLAIM TO EARLIER APPLICATION

This application claims priority to U.S. Provisional Patent Application No. 61/517,870, filed Apr. 27, 2011, and is a continuation-in-part of co-pending nonprovisional application Ser. No. 12/018,703, filed Jan. 23, 2008, which claims priority to provisional application Ser. No. 60/981,414, filed Oct. 19, 2007, and is a continuation-in-part of co-pending nonprovisional application Ser. No. 11/759,219, filed March, 2007, all of which are incorporated herein by reference.

FIELD OF THE INVENTION

This invention relates to the field of spinal fusion. In particular, this invention is drawn to spinal fusion devices and associated methods.

BACKGROUND OF THE INVENTION

The spine can be considered to be a series of movable segments made up of vertebrae and discs. Due to trauma, disease, and/or aging, the spine may be subject to degeneration. This degeneration may destabilize the spine and cause pain and/or nerve damage. Medical procedures are often required to either ease back pain, repair damage, or to prevent future damage.

One procedure that is often used to treat back pain or spinal damage is spinal fusion. Spinal fusion is a surgical technique used to combine two or more adjacent vertebrae. Supplemental bone tissue is used in conjunction with the patient's natural osteoblastic processes in a spinal fusion procedure. Spinal fusion is used primarily to eliminate back pain caused by the motion of the damaged vertebrae by immobilizing adjacent vertebrae. Conditions for which spinal fusion might be done include degenerative disc disease, treatment of a spinal tumor, a vertebral fracture, scoliosis, degeneration of the disc, spondylolisthesis, or any other condition that causes instability of the spine.

One problem with prior art spinal fusion techniques relates to device migration. For example, prior to complete bone fusion, a fusion device may migrate from the desired position. In examples where bone screws are used, the insertion and tightening of the bone screws tends to cause device migration. Another problem with typical prior art fusion techniques is that fusion devices, or associated plates or fasteners, protrude from the spine, causing discomfort, damage, or danger to surrounding vascular or neurological tissues.

There is therefore a need for spinal fusion devices and related spinal fusion procedures that adequately treats degenerative disc disease and other spinal conditions, while providing improvements over the prior art.

SUMMARY OF THE INVENTION

An apparatus of the invention provides a spinal fusion device including a fusion bearing device configured to fit between two adjacent vertebrae, and a retention device configured to be secured to at least one of the adjacent vertebrae to prevent migration of the fusion bearing device, wherein the retention device has a height that is less than the height of the fusion bearing device.

One embodiment of an interbody fusion device includes a first piece configured to be placed between adjacent vertebrae, a second piece configured to at least partially fit within the first piece when the first piece is inserted between adjacent vertebrae, and one or more fastening devices for securing the second piece to at least one of the adjacent vertebrae.

Another embodiment of the invention provides a spinal fusion device including a fusion bearing device configured to fit between two adjacent vertebrae, a retention device configured to prevent migration of the fusion bearing device, wherein the retention device has a height that is less than the height of the fusion bearing device, one or more fasteners coupled to the retention device to compress the two adjacent vertebrae to the fusion bearing device.

Another embodiment of the invention provides a method of fusing adjacent vertebrae including providing an interbody fusion device, inserting the interbody fusion device between two adjacent vertebrae, providing a retention device configured to fit within the interbody fusion device, sliding the retention device into the interbody fusion device, and securing the retention device to at least one of the adjacent vertebrae.

In another broad respect, this invention is a spinal fusion device comprising: a fusion component configured to fit between two adjacent vertebrae; and an anterior plate configured to couple the fusion component using mated snap on members located where the fusion component and anterior plate meet to couple and wherein the anterior plate is to be secured to at least one of the adjacent vertebrae to prevent migration of the fusion component. The spinal fusion device can have a fusion component generally conforms to the contour of the adjacent vertebrae, further comprise one or more fasteners for securing the anterior plate to at least one of the adjacent vertebrae, can be configured so that each fastener devices are inserted through a bore formed in the anterior plate, can be configured so that the fasteners are bone screws, can be configured so that the fusion component has a hollow center portion adapted to receive a material to enhance spinal fusion, can be configured to that the snap on members provide a hinge so that the anterior plate and the fusion component can pivot about the snap on member; further comprise an anti-backout mechanism coupled to the anterior plate to prevent fastener migration, be configured such that the fusion component is horseshoe-shaped, be configured so that the the mated snap members comprise a male member having a lip that is configured to slide over a projection of a female snap member into groove which is configured to lock the anterior plate and fusion component together, configured such that an opening exists between the anterior plate and fusion component when coupled that permits rotation/pivot, and including but not limited to any combination thereof.

In another broad respect, this invention is a method of fusing adjacent vertebrae: inserting a fusion component between two adjacent vertebrae; coupling an anterior plate to the fusion component, wherein the anterior plate and the fusion component each have complementary snap members that couple the anterior plate and fusion component together; and securing the anterior to at least one of the adjacent vertebrae.

In another broad respect, this invention is a method of manufacturing a spinal fusion kit, comprising: providing a fusion component configured to fit between two adjacent vertebrae; and providing an anterior plate configured to couple the fusion component using mated snap on members located where the fusion component and anterior plate meet to couple and wherein the anterior plate is to be secured to at least one of the adjacent vertebrae to prevent migration of the fusion component.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which:

FIG. 17 shows the device of FIGS. 12-13 where a threaded rod is attached. The rod serves to position the fusion component and guide the anterior plate to the fusion component. The rod can thereafter be removed or sheered off at the anterior plate.

DETAILED DESCRIPTION

The present invention relates to spinal fusion implants and related spinal fusion procedures for use in lumbar and especially cervical applications. One type of spinal fusion is interbody fusion. Typically, an interbody fusion procedure places a bone graft between the vertebra in the area normally occupied by an intervertebral disc. In preparation for a spinal fusion procedure, the intervertebral disc is removed entirely. A device may be placed between the vertebra to maintain spine alignment and disc height. Fusion then occurs between the endplates of the vertebrae. In some examples, fusion is augmented by a process called fixation, meaning the placement of screws, rods or plates to stabilize the vertebra to facilitate bone fusion. The present invention provides an interbody fusion device that overcomes problems found in the prior art.

Generally, the present invention provides a two piece interbody fusion device that may be used with anterior cervical or lumbar interbody fusion. In one example, a first piece of the interbody fusion device is a U-shaped load bearing device that is designed to bear the axial loading from the end plates of adjacent vertebrae. A second piece of the interbody fusion device is a retention device whose function is to prevent migration of the load bearing device. One or more fasteners, such as bone screws secure the retention device to the vertebrae above and below the load bearing device. The fasteners cause the end plates of the vertebrae to compress the end plates to the load bearing device to facilitate proper fusion. If desired, the fasteners may include an anti-backout mechanism.

Figure 1:
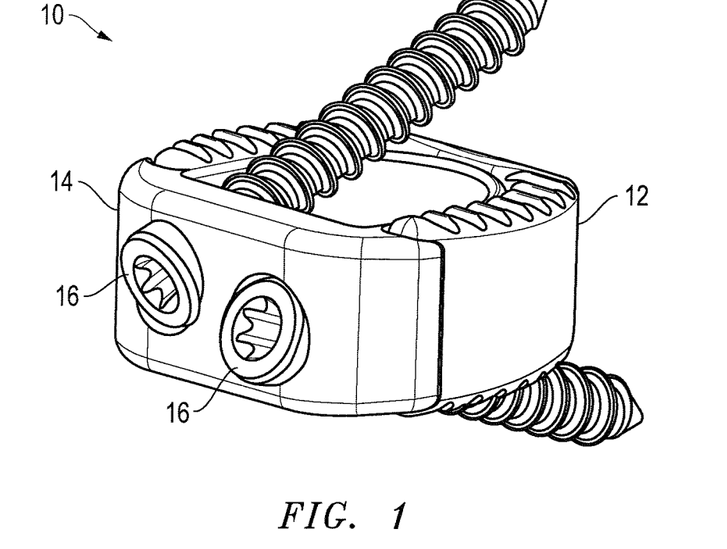
FIG. 1 is an isometric view of one example of an interbody fusion device of the present invention.

FIG. 1 is an isometric view of one example of an interbody fusion device of the present invention. FIG. 1 shows an interbody fusion device 10. The interbody fusion device 10 includes a load bearing device 12, a retention device 14, and two bone screws 16, each of which are described in more detail below.

Figure 2:
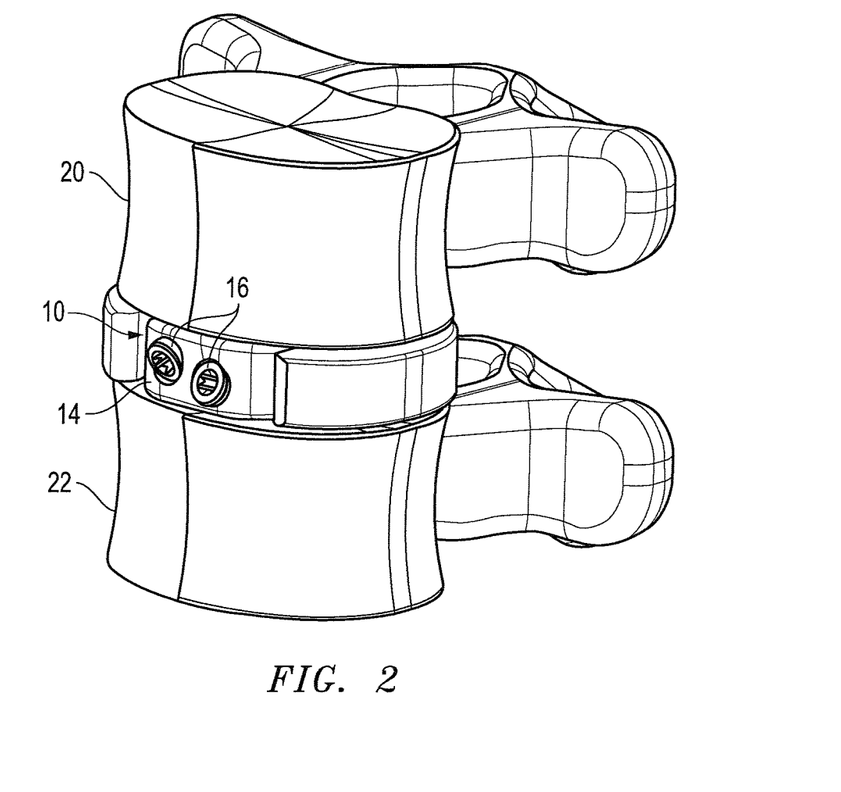
FIG. 2 is an isometric diagram of the interbody fusion device shown in FIG. 1 installed between the end plates of two adjacent vertebrae.

FIG. 2 is an isometric diagram of the interbody fusion device 10 shown in FIG. 1 installed between the end plates of two adjacent vertebrae 20 and 22 to facilitate the fusion of the vertebrae 20 and 22. The interbody fusion device 10 provides load bearing support as well as the proper spacing between the vertebrae 20 and 22 while fusion of the vertebrae takes place. As described in more detail below, the interbody fusion device 10 is positioned between the end plates of the vertebrae 20 and 22 within the vertebral body in the area usually occupied by the intervertebral disc.

Figure 3:
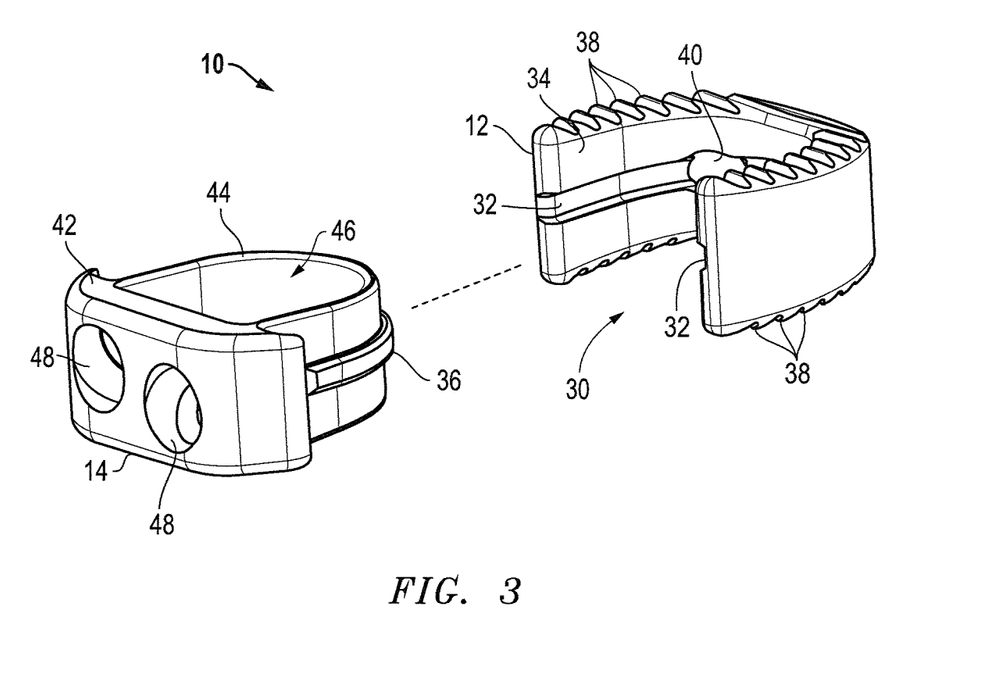
FIG. 3 is an exploded view of an interbody fusion device, showing a load bearing device and a retention device.

FIGS. 3-6 are views illustrating various details of one example of an interbody fusion device of the present invention. FIG. 3 is an exploded view of the interbody fusion device 10, showing the load bearing device 12 and the retention device 14 separately. The load bearing device 12 is a generally U-shaped device having an open end 30 that is configured to receive the retention device 14 (described below). A groove 32 is formed around the interior surface 34 of the load bearing device 12. A corresponding tongue 36 is formed around the outside surface of the retention device 14 such that, when the retention device 14 is inserted within the open end 30 of the load bearing device 12, the tongue 36 and groove 32 tend to hold the retention device 14 in a desired position, relative to the load bearing device 12.

The load bearing device 12 also includes a plurality of ridges 38 formed on the top and bottom ends of the device 12. The ridges 38 are angled and come to a point in such a way that the ridges 38 help to hold the load bearing device 12 to the end plates of the vertebrae to reduce the chance of anterior migration of the implant. If desired, one or more openings 40 can be formed in the load bearing device 12 to facilitate instrumentation devices. In the example shown in FIG. 3, two openings 40 are formed on opposite sides of the load bearing device 12 (the second opening 40 is hidden in FIG. 3). An implant holder can be used to insert the load bearing device 12 into a vertebral body using the openings 40.

The retention device 14 has a front portion 42 and a rear portion 44 that, together, form a hollow body 46. The hollow body 46 provides a relatively large graft volume, compared to a typical ALIF or ACDF allograft. Prior to insertion into the load bearing device 12, the hollow body 46 of the retention device 14 can be filled with a prepared material that will help to facilitate fusion of the vertebrae (see FIGS. 9-10). Examples of a material include allograft bone, autograft bone, bone marrow, bone morphonogenic protein (BMP), Autologous Stem Cells, etc., to facilitate fusion through opening 46.

The retention device 14 is shaped to such that it will fit within the open end 30 of the load bearing device 12. In the example shown in FIG. 3, two holes 48 are formed in the front portion 42, and are adapted to received fasteners, such as bone screws, pegs, etc. One of the holes 48 is angled down, and the other hole 48 is angled up, such that a first fastener can be secured to the vertebra above the interbody fusion device 10, and a second fastener can be secured to the vertebra below the interbody fusion device 10 (described in more detail below).

Figure 4:
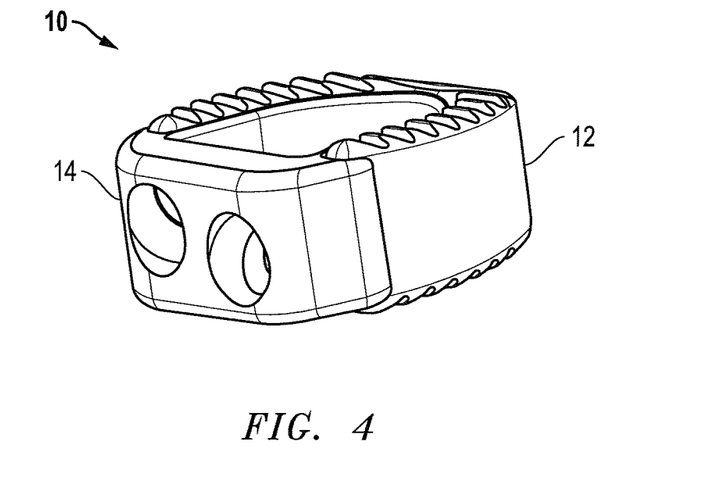
FIG. 4 is an isometric diagram of the interbody fusion device shown in FIG. 3 with the retention device inserted into the load bearing device.

FIG. 4 is an isometric diagram of the interbody fusion device 10 shown in FIG. 3 with the retention device 14 inserted into the load bearing device 12. As shown, the retention device 14 fits within the load bearing device 12. The resulting assembly provides a load bearing structure that is safely secured in place without any fasteners having to be placed directly into the load bearing device 12. FIG. 4 also illustrates that the height of the retention device 14 is less than the height of the load bearing device 12. As a result, all of the load on the vertebrae will be placed on the load bearing device 12, and not on the retention device 14. At the same time the load bearing device 12 is securely is the position desired by the surgeon. In some prior art devices, the fastening mechanisms (e.g., cervical plates with screws, spacers held in place by off-set screws, etc.), will bear some of the load, increasing the likelihood of device failure or migration. In addition, with typical prior art devices, a spacer is likely to migrate or twist slightly as bone screws are tightened by the surgeon. With the interbody fusion device 10 of the present invention, the load bearing structure will remain stationary, even as bone screws are tightened to secure the retention device in place.

Figure 5:
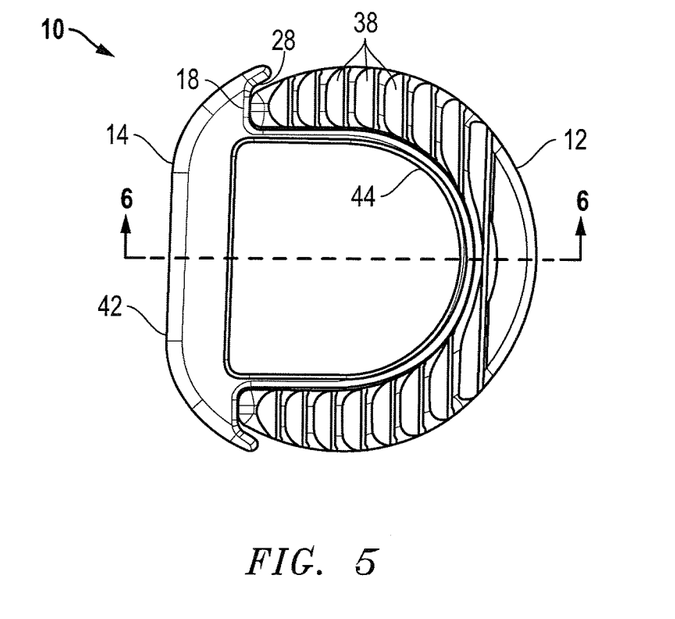
FIG. 5 is a top view of the assembled interbody fusion device shown in FIG. 4.

FIG. 5 is a top view of the assembled interbody fusion device 10 shown in FIG. 4. As shown, when the load bearing device 12 and retention device 14 are put together, the interbody fusion device 10 has a generally round profile, that substantially fits within a vertebral body (shown in more detail below). FIG. 5 also illustrates how the load bearing device 12 is securely held in place by the retention device 14, such that anterior and lateral migration is prevented. Also note that that trailing edges 18 of the load bearing device 12 are nested and contained in pockets 28 formed in the retention device 14. This further secures the load bearing device 12 in place.

Figure 6:
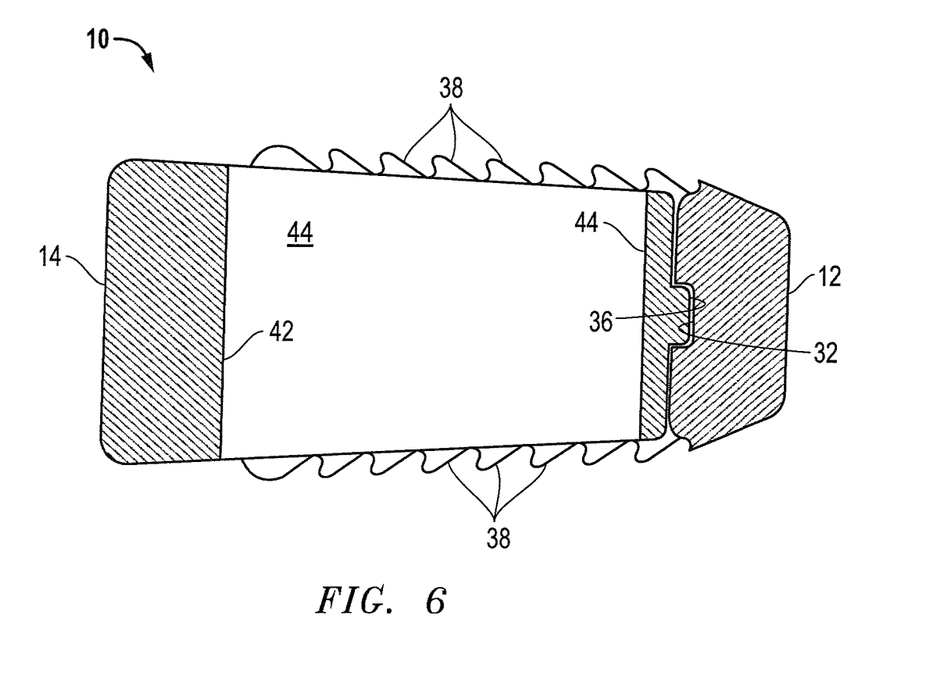
FIG. 6 is a sectional diagram taken along line 6-6 of FIG. 5.

FIG. 6 is a sectional diagram taken along line 6-6 of FIG. 5. FIG. 6 shows the retention device 14, including the front portion 42 and the rear portion 44, which forms the hollow body 46. The tongue 36 of the retention device 14 fits within the groove 32 of the load bearing device 12. FIG. 6 also more clearly illustrates that the height of the load bearing device 12 is greater than the height of the retention device 14. As a result, the load bearing device 12 will be the structure (primarily, the ridges 38) that engages the end plates of the vertebrae, thus supporting the axial loading of the vertebrae.

Figure 7:
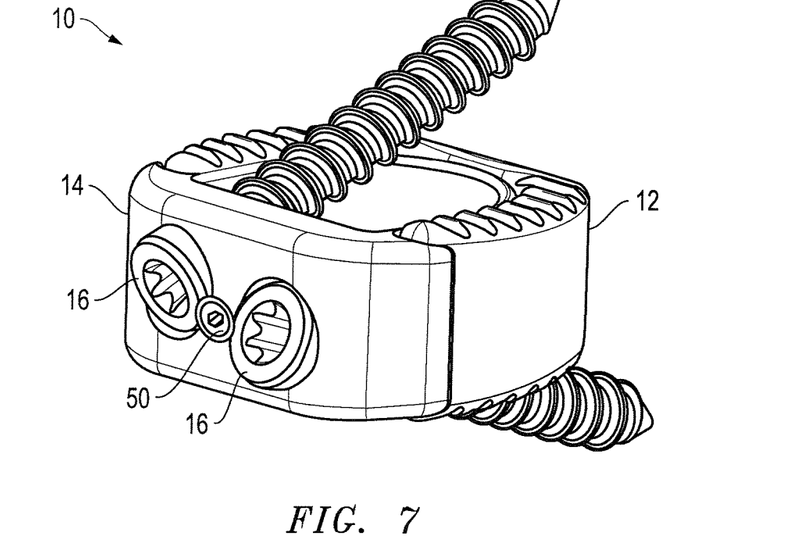
FIG. 7 is an isometric diagram of an interbody fusion device utilizing an anti-backout mechanism.

As mentioned above, the bone screws 16 may include an anti-backout mechanism. FIG. 7 is an isometric diagram of the interbody fusion device 10 utilizing an anti-backout mechanism. In this example, the anti-backout mechanism is comprised of a set screw 50, which can be screwed into the front portion of the retention device 14. The set screw in this example includes a driver socket for receiving a driver, which may be used by a surgeon to tighten the set screw 50. Of course, any desired type of anti-backout device may also be used.

As was shown in FIG. 2, a interbody fusion device of the present invention is intended to be installed between the end plates of two adjacent vertebrae to facilitate the fusion of the vertebrae. FIGS. 8-11 further illustrate the installation of an interbody fusion device of the present invention between adjacent vertebrae.

Figure 8:
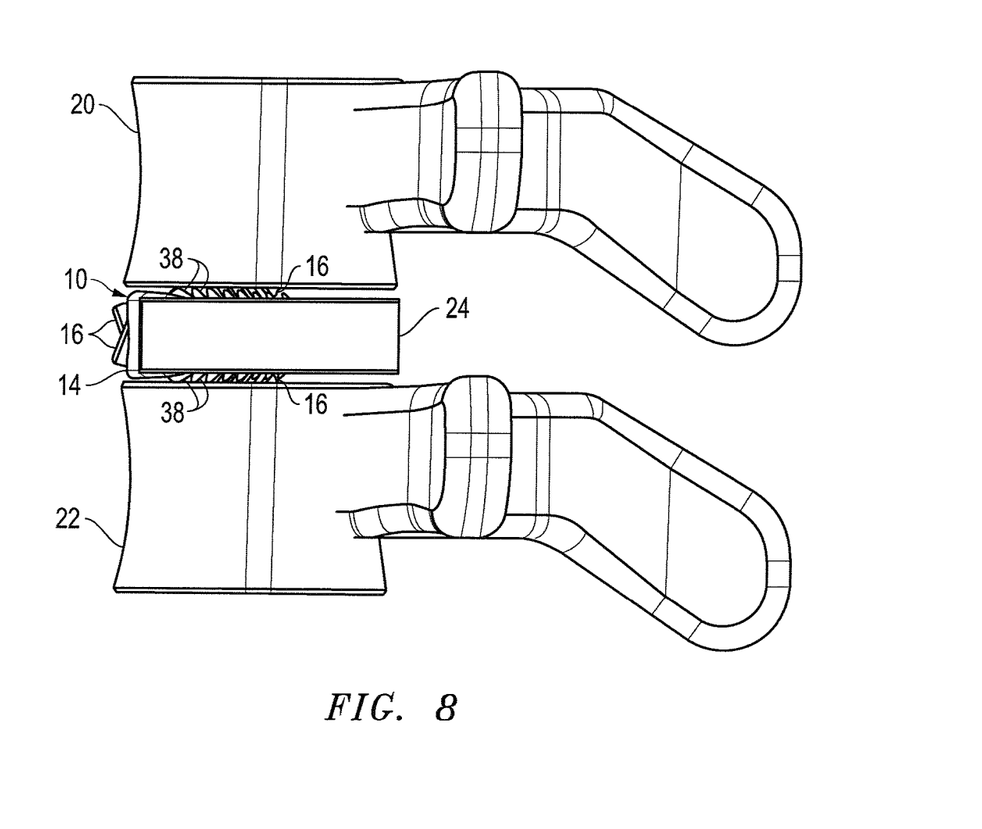
FIG. 8 is a side view of the interbody fusion device and vertebrae shown in FIG. 2.

FIG. 8 is a side view of the interbody fusion device 10 and vertebrae shown in FIG. 2. As shown in FIG. 8, the interbody fusion device 10 has a zero-profile anteriorly. In other words, the interbody fusion device 10 has a shape (e.g., see FIG. 5) in the axial plane that substantially fits within the perimeter defined by the vertebrae. In typical prior art devices, a cervical plate, or similar structure, is affixed to the side of the vertebrae, creating an extending profile that can cause discomfort, or damage to nearby tissue. Also note from FIG. 8 that the interbody fusion device 10 (not including the bone screws 16) also does not extend beyond (above or below) the end plates of the vertebrae.

Prior to the insertion of the interbody fusion device 10, the intervertebral disc is removed, so the interbody fusion device 10 can be place between the vertebrae 20 and 22. In one example, a window is cut in the disc annulus 24. Next, portions of the nucleus pulposus 26 (FIGS. 9, 10) are removed so that the interbody fusion device 10 can fit between the vertebrae 20 and 22 as shown in the figures.

Figure 9:
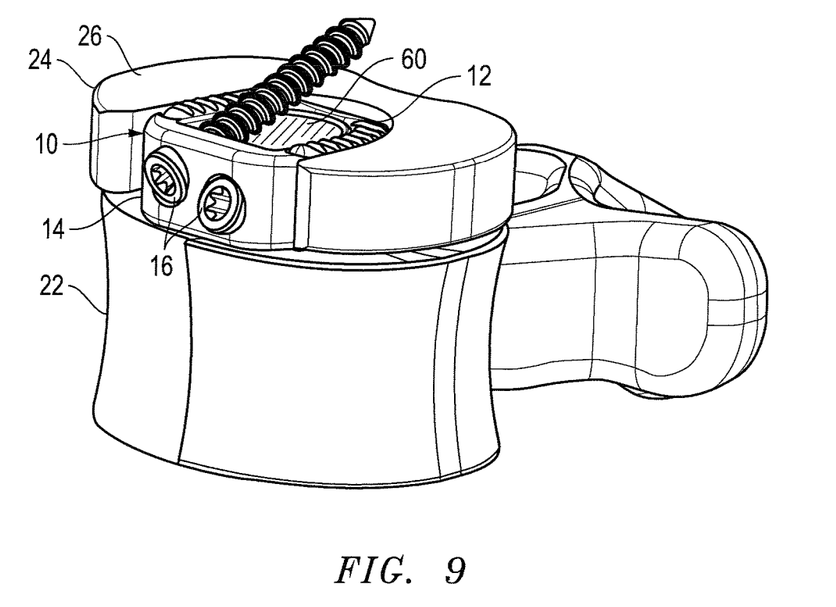
FIG. 9 is an isometric view similar to FIG. 2, but with the upper vertebra removed.
Figure 10:
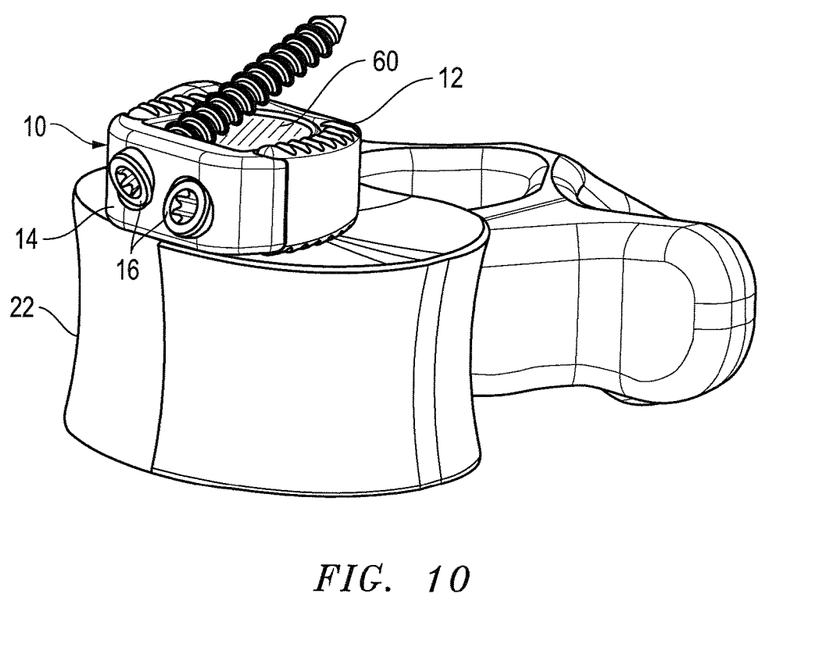
FIG. 10 is an isometric view similar to FIG. 9, but with the disc annulus and nucleus pulpous removed.
Figure 11:
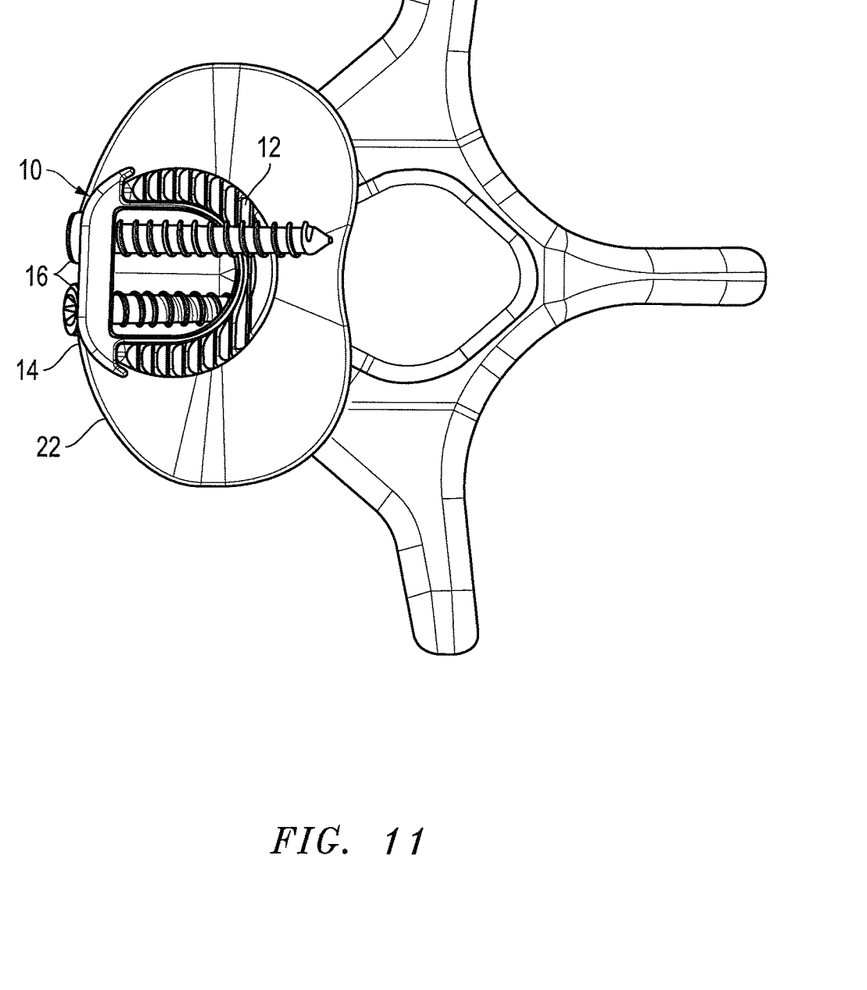
FIG. 11 is a top view of the interbody fusion device and vertebral body shown in FIG. 10.

FIG. 9 is an isometric view similar to FIG. 2, but with the vertebra 20 removed to illustrate how the interbody fusion device 10 is positioned relative to the vertebrae and disc annulus 24. FIG. 9 shows the disc annulus 24 with a portion removed to allow the interbody fusion device 10 to be inserted. FIG. 9 also shows the remaining nucleus pulpous 26 surrounding the interbody fusion device 10. FIG. 10 is an isometric view similar to FIG. 9, but with the disc annulus 24 and nucleus pulpous 26 removed to further illustrate how the interbody fusion device 10 is positioned relative to the vertebrae and disc annulus 24. FIGS. 9 and 10 also include shading, which represents fusion material 60, described above. FIG. 11 is a top view of the interbody fusion device 10 and vertebral body shown in FIG. 10. Note that, for clarity, the material 60 is not shown in FIG. 11.

FIGS. 12-21 illustrate another embodiment of the invention, which is primarily configured and adapted for use as a 2-piece cervical interbody fusion device. The devices can be reversible, meaning they can be used with either side facing up. The term "anterior plate" in general has the same meaning as "retention device" as used herein. The anterior plate is also sometimes referred to as a face plate or rescue plate. In certain embodiments the anterior plate includes one or two lips. The term "fusion component" generally has the same meaning as "fusion bearing device." The use of the term component is used to differentiate the piece from the spinal fusion device as a whole. The term "lip" as used herein for the portion of the anterior plate that abuts the apophyseal ring can also be referred to as a "ledge."

Figure 12:
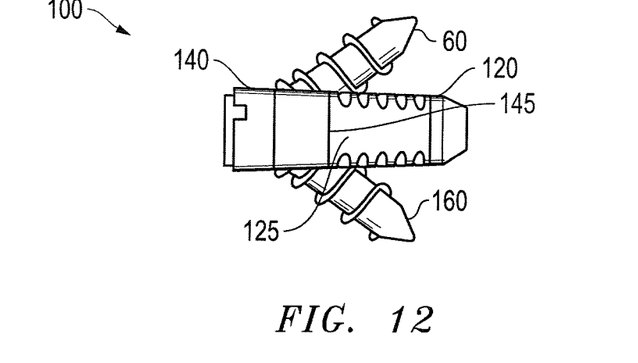
FIGS. 12 and 13 show side and overhead views of a zero profile embodiment of this invention with two fasteners.

FIG. 12 is a side view of the spinal fusion device 100, which includes a fusion component 120, an anterior plate (retention device) 140, and two or more fasteners 160. The device is zero profile. Female and male snap elements 125 and 145 are at the point of attachment between the fusion component 120 and the anterior plate 140. The snap elements 125 and 145 enable the fusion device 120 and anterior plate 140 to swivel a given number of degrees, which aids a surgeon in lining up the spinal fusion device 100 between cervical vertebrae. Thus the elements 125, 145 are configured to provide both a snap-in capability and a hinge to give the surgeon an aid to position the device. The snap members/elements serve to provide an axis about which the anterior plate may pivot (or "flex," "wobble," or "turn") prior to the fasteners securing the anterior plate in place.

Figure 13:
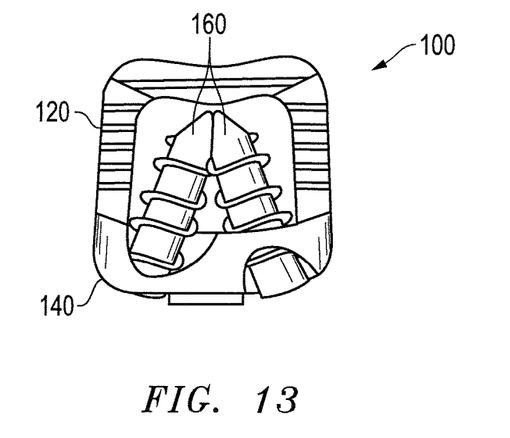
Figure 14:
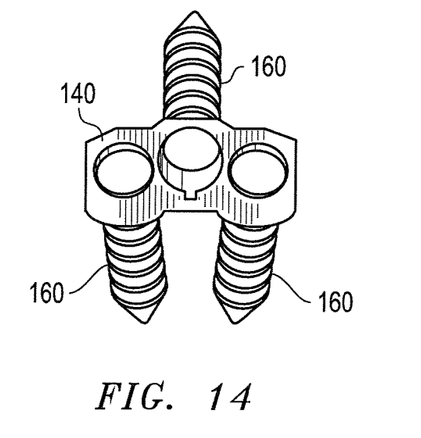
FIGS. 14 and 15 show front and overhead views of an embodiment of this invention with three fasteners.
Figure 15:
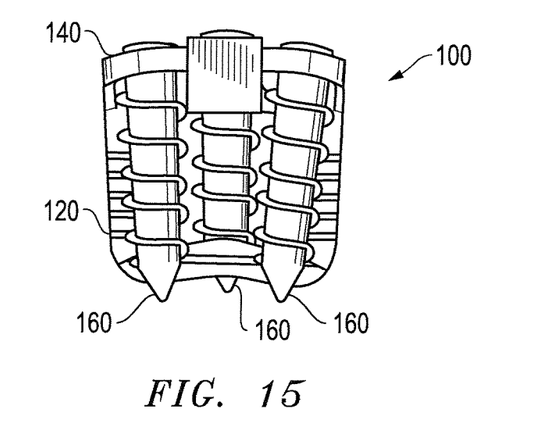

FIGS. 13-15 illustrate different configurations as to how the fasteners 160 can be screwed into a bone. Thus in FIG. 13 a top-down view is shown where there are two fasteners 160 that extend through bores in the anterior plate 140, each angled toward the center of the spinal fusion device 100, with one angled away from the viewer and one angled toward the view. FIGS. 14-15 depict a side view of a portion of an anterior plate 140 with fasteners 160 extending through bores in the plate. FIG. 14 illustrates a three fastener configuration with two fasteners 160 angled downward toward one vertebrae and one fastener 160 angled up toward the other vertebrae during use. It should be appreciated that the bores in the anterior plate 140 are machined to provide the given angles of entry for the bores. FIG. 15 is a top down view of the spinal fusion device 100 with the configuration of FIG. 14.

Figure 16:
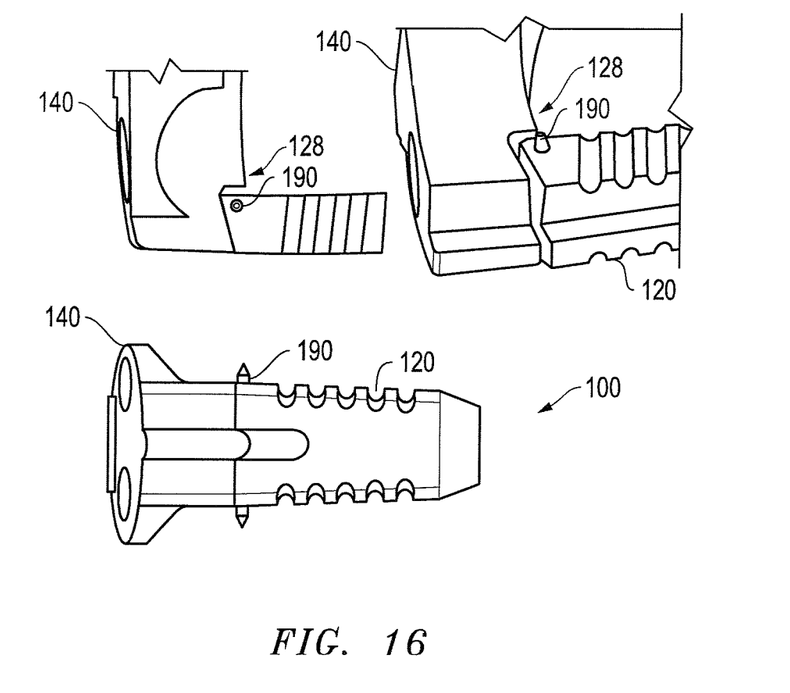
FIG. 16 shows the snap-in element of FIGS. 14 and 15.

FIG. 16 illustrates an embodiment where the fusion device 120 includes one or more sharp protrusions 190 sized and adapted to secure the device 100 within the disc space. The protrusions 190 can be on the fusion component 120, the anterior plate 140, or both, and can be placed anywhere as desired on the top and bottom faces of the spinal device 100. The protrusions 190 can be made of metallic or radiolucent materials.

Figure 17:
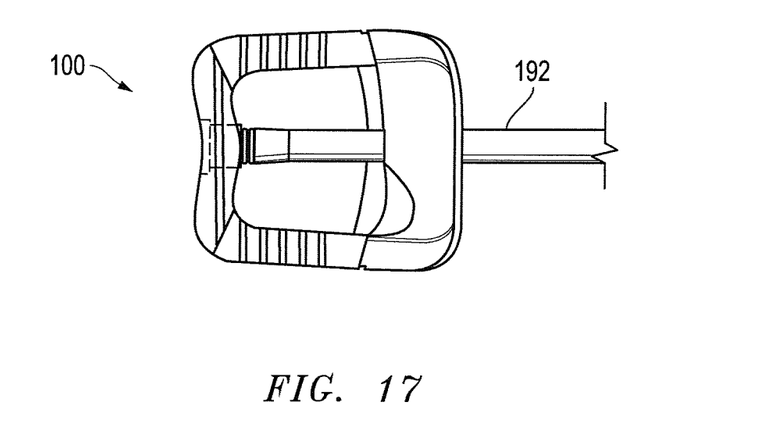

FIG. 17 shows a spinal fusion device 100 (cage) attached to a guide rod 192 to facilitate placement and assembly. The rod can be unscrewed and removed after placement. Alternatively, the rod can be sheered off at the anterior plate, such as by use of notching or a separate tool used to break off the section protruding out of the anterior plate.

Figure 18:
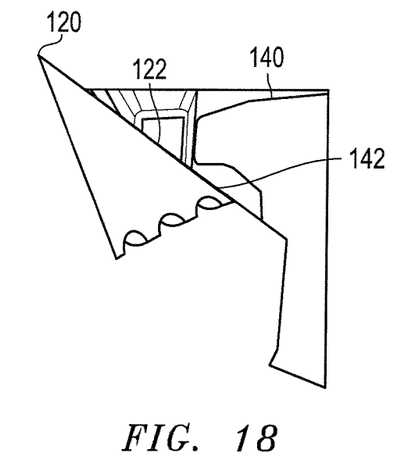
FIG. 18 shows on embodiment of the snap element of this invention.

FIG. 18 shows the snap elements in more detail. In this embodiment, the male snap element 142 is placed on the anterior plate 140, and corresponds to a female element 122 on the fusion component 120. Typically there will be such snap elements on both sides of the anterior plate 140 and fusion component 120. It should be appreciated that, alternatively, the male elements can be placed on the fusion component 120 and the female elements placed on the anterior plate 140. Also depicted in FIG. 18 is an optional shelf/lip 145 positioned on the anterior plate 140 for abutment with an apophyseal ring of a cervical vertebrae. As subsidence is most commonly seen on the inferior portion of the plate 140 the shelf 145 is depicted in that direction; however, there may be a shelf on either the inferior or superior side of the plate 140, or both sides of the plate 140.

Figure 19:
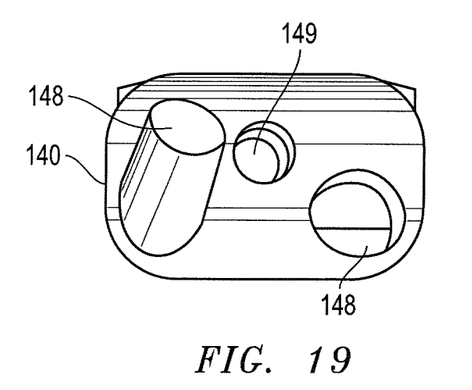
FIGS. 19-20 shows an embodiment of this invention wherein the anterior plate includes a shelf.

FIG. 19 illustrates a front view of the anterior plate 140, showing the bores 148 for fasteners as well as a bore 149 that can be used with the guide rod 192 and/or a locking mechanism. Bore 148 is on the lip 145 (or "ledge"). The lip 145 allows the fastener to penetrate apothyseal ring bone at a lower angle than needed for the fastener such as in FIG. 1 which may require a relatively high angle of approach in order to penetrate the end plates of the vertebrae.

Figure 20:
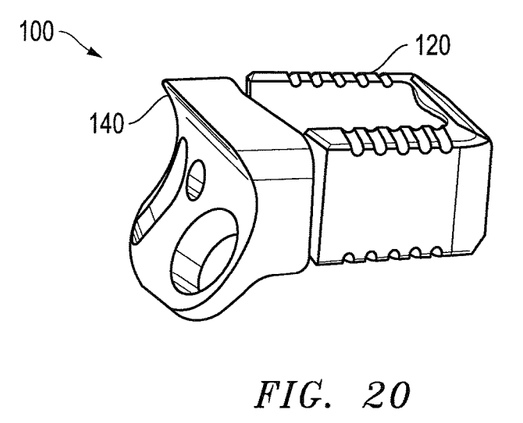

FIG. 20 illustrates a perspective view of the cervical fusion device 100, with the anterior plate 140 and fusion component 120 linked together, but without fasteners protruding through the bores 148. Such a locking mechanism can be of conventional design, being integral with the anterior plate 140 or being a separately attachable. The snap-on mechanism is also depicted in FIG. 20.

The anterior plate 140 can include a ledge on the posterior side of the anterior plate that comes into alignment with the fusion component 120, with the ledge configured to limit or eliminate side to side hinging of the plate and fusion body (as distinguished from the snap elements which permit up and down hinging (in the inferior and superior directions). Such an element 128 is partially depicted in FIG. 16.

Figure 21:
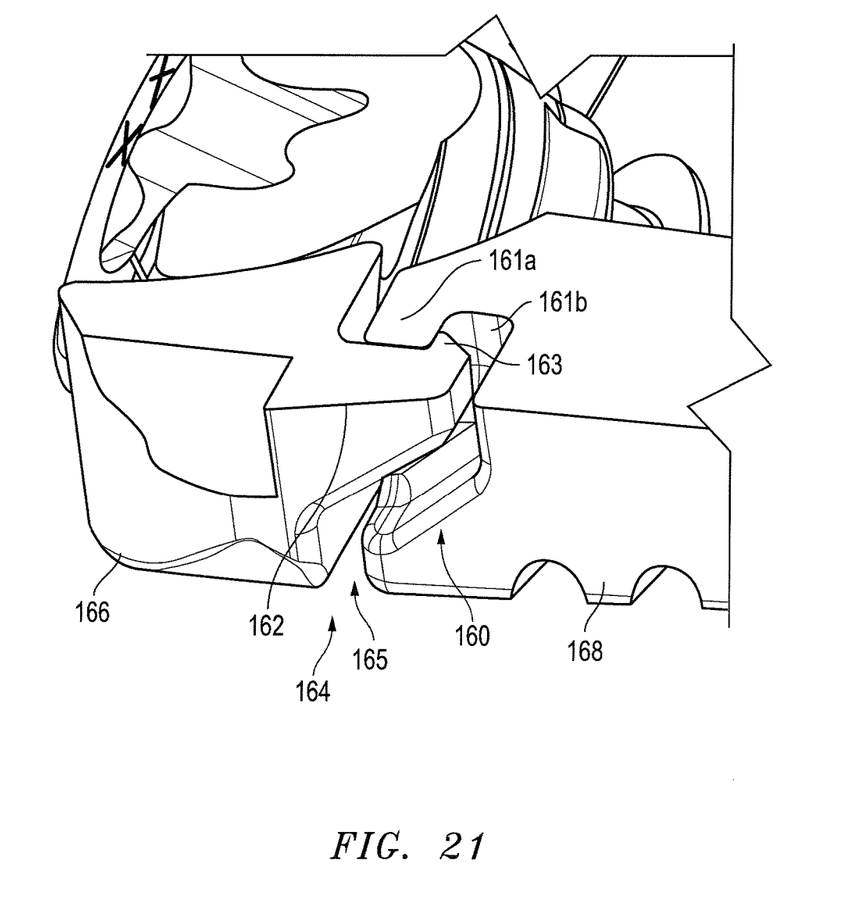
FIG. 21 shows another embodiment of the snap mechanism of this invention.

FIG. 21 shows another embodiment of the snap on member of this invention. The snap element 164 includes a female snap locking configuration 160 that receives male snap locking feature 162. The two pieces snap together when pressure is applied against anterior plate 166 to force the tip 163 of male member 162 to slide over the projection (or step, ledge, and the like) 161a and into groove (or track, opening, and the like) 161b of horseshoe shaped fusion component 168 to thereby lock the anterior plate into place. The configuration includes an opening 165 that permits rotation/pivot. Alternatively, the male snap element can be on the fusion component and the female snap element can be on the anterior plate.

Figure 22:
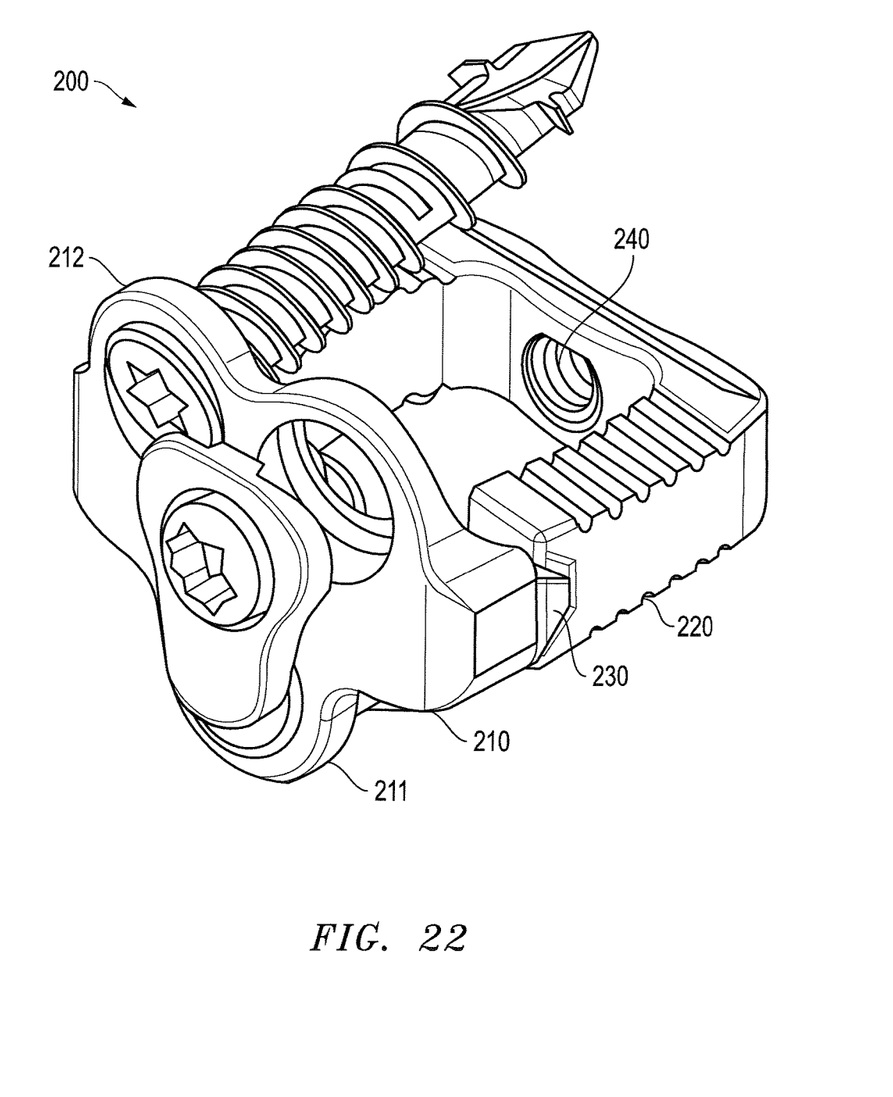
FIG. 22 shows another embodiment of the spinal fusion device with a three-bore anterior plate having inferior and superior lips as well as another embodiment of the locking mechanism.

FIG. 22 shows another embodiment of the spinal fusion device 200 with a three-bore anterior plate 210 having inferior and superior lips 211, 212 as well as another embodiment of the locking mechanism 280. The anterior plate 210 attaches/couples to horseshoe-shaped (or "U-shaped") fusion component 220 via snap members 230 (one not shown). The lips permit a lower angle of approach for engaging the fasteners with the vertebrae as compared to an anterior plate that has a zero profile. An optional threaded bore 240 is also shown coupling with a guide rod such as shown in FIG. 17.

Figure 23:
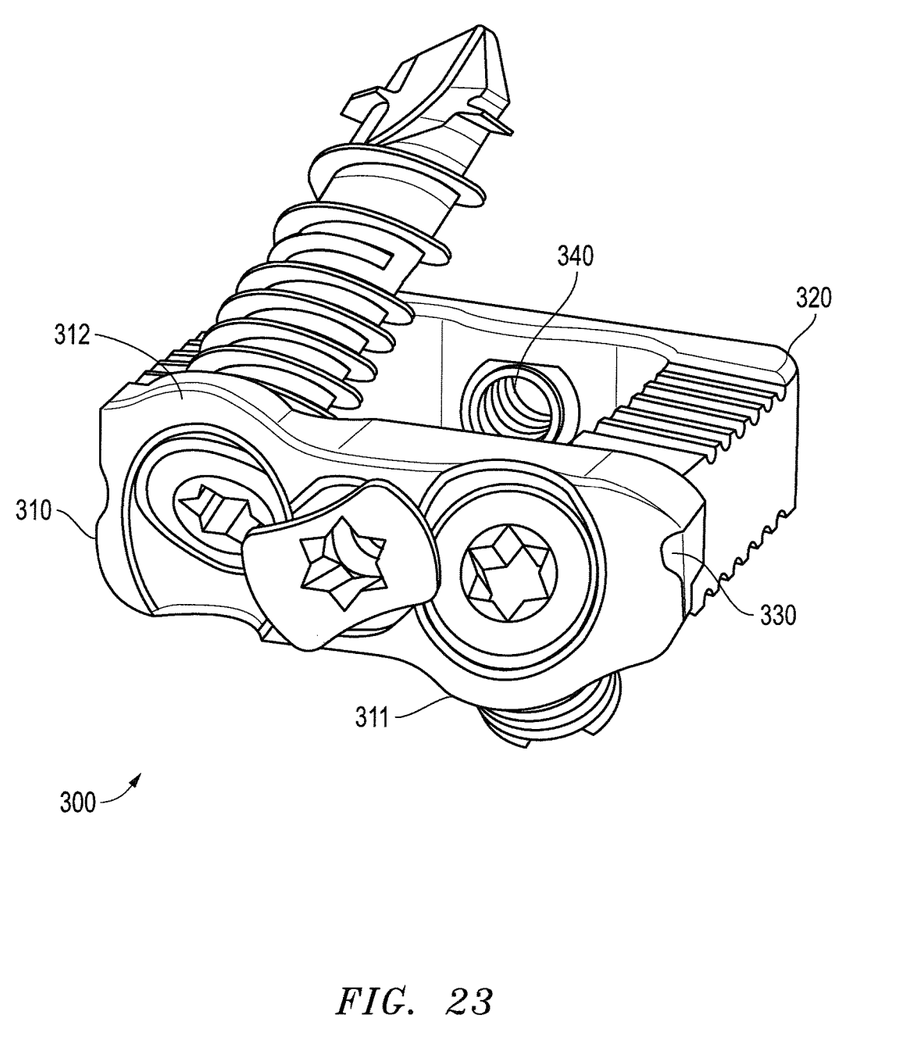
FIG. 23 shows another embodiment of the spinal fusion device with a two-bore anterior plate having inferior and superior lips that are not as prominent as the lips as shown in FIG. 22.

FIG. 23 shows another embodiment of the spinal fusion device with a two-bore anterior plate 310 having inferior and superior lips 311, 312 that are not as prominent as the lips as shown in FIG. 22. In his embodiment the anterior plate 310 attaches/couples to horseshoe-shaped (or "U-shaped") fusion component 320 via snap members 330 (one not shown). The lips permit a lower angle of approach for engaging the fasteners with the vertebrae as compared to an anterior plate that has a zero profile. The profile of this embodiment is less than the profile of the embodiment of FIG. 22.

Following is an example of how an interbody fusion device of the present invention may be used in an ALIF or ACDF spinal fusion procedure, or any other spinal fusion procedure. As described above, a window is cut in the anterior side of the disc annulus 24 (FIG. 9) to allow an interbody fusion device to be inserted. Next, the nucleus pulposus 26 is cleaned out to provide room for the interbody fusion device. Next, a load bearing device 12 of the desired size (e.g., having a height to get the desired spacing between the vertebrae) is inserted between the end plates of the adjacent vertebrae using the appropriate instrumentation. During these procedures, the retention device 14 can be prepared with a desire material 60 placed in the hollow body 46. Once the surgeon is satisfied that the load bearing device is in the ideal position, the retention device 14 is inserted into the load bearing device 12, with the tongue 36 and groove 32 guiding the retention device 14. Note that, because the height of the retention device is less than the height of the load bearing device, the retention device 14 can slide into the load bearing device 12 without interfering with the relative placement of the load bearing device 12 and the end plates of the adjacent vertebrae. Also, the retention device 14 is stress shielded and is not axial loaded by the vertebrae. Once the retention device is in place, the bone screws 16 can be installed through the openings 48 and into the vertebrae. As the bone screws 16 are tightened, the vertebrae will compress vertebral bodies 20 and 22 onto the load bearing member 12, which will help facilitate fusion. Also, since the bone screws 16 secure the retention device 14, and do not directly secure the load bearing device 12, the bone screws will not tend to cause the interbody fusion device 10 to migrate. If desired, an anti-backout mechanism (such as the set screw 50 shown in FIG. 7) can be used to prevent the bone screws 16 from loosening.

The interbody fusion device of the present invention can be made from any desired materials. In one example, the load bearing device is made from PEEK (or a similar material), bone, metal, or any other structural substitute. In one example, the retention device is made from PEEK (or a similar material), bone, metal, or any other structural substitute. If the components of the interbody fusion device are radiolucent (such as with PEEK), then doctors will be able monitor the fusion process better with X-rays.

An interbody fusion device of the present invention may be configured to any desired size or shape. In one example, load bearing devices can be provided in multiple thicknesses, allowing a surgeon to select a desired size (e.g., 10.5 mm, 12.5 mm, 14.5 mm, 16.5 mm, 1.5 mm, etc.). In the examples shown in the figures, the load bearing device has about 6° of lordosis (e.g., see FIG. 6). Of course any desired angle could be used.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

What is claimed is:

1. A spinal fusion device comprising: a fusion component configured to fit between two adjacent vertebrae, wherein the fusion component is a load bearing device; a stress shielded anterior plate configured to couple the fusion component using mated snap on members located where the fusion component and anterior plate meet to couple and wherein the anterior plate is to be secured to at least one of the adjacent vertebrae to prevent migration of the fusion component, wherein a height of the anterior plate is less than a height of the fusion component, wherein the anterior plate does not contact end plates of the vertebrae, and wherein the spinal fusion device has a shape that is zero-profile anteriorly, and further wherein the fusion component has a groove around its interior surface and the anterior plate has a tongue around its outside surface such that, when the anterior plate is inserted within an open end of the fusion component, the tongue and groove hold the anterior plate in a desired position, relative to the fusion component; one or more fasteners for securing the anterior plate to at least one of the adjacent vertebrae; and an anti-backout mechanism coupled to the anterior plate to prevent fastener migration, wherein the anti-backout mechanism comprises a locking plate and said locking plate comprises at least two opposing protrusions that extend outward from the plate and are positioned over the ends of the one or more fasteners and prevent the one or more fasteners from backing out.

2. The spinal fusion device of claim 1, wherein the fusion component generally conforms to the contour of the adjacent vertebrae.

3. The spinal fusion device of claim 1, wherein each fastener is inserted through a bore formed in the anterior plate.

4. The spinal fusion device of claim 1, wherein the one or more fasteners are bone screws.

5. The spinal fusion device of claim 1, wherein the fusion component has a hollow center portion adapted to receive a material to enhance spinal fusion.

6. The spinal fusion device of claim 1, wherein the snap on member provides a hinge so that the anterior plate and the fusion component can pivot about the snap on member.

7. The spinal fusion device of claim 1, wherein the fusion component is horseshoe-shaped.

8. The spinal fusion device of claim 1, wherein the mated snap members comprise a male member having a lip that is configured to slide over a projection of a female snap member into a groove which is configured to lock the anterior plate and fusion component together.

9. The spinal fusion device of claim 8, wherein an opening exists between the anterior plate and fusion component when couple that permits rotation/pivot.

\* \* \* \* \*